US009867950B2

(12) United States Patent
Takemoto

(10) Patent No.: US 9,867,950 B2
(45) Date of Patent: Jan. 16, 2018

(54) SYRINGE ASSEMBLY, SYRINGE ASSEMBLY PACKAGE BODY, AND PRE-FILLED SYRINGE

(71) Applicant: Terumo Kabushiki Kaisha, Tokyo (JP)

(72) Inventor: Masafumi Takemoto, Fujinomiya (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 288 days.

(21) Appl. No.: 14/641,263

(22) Filed: Mar. 6, 2015

(65) Prior Publication Data
US 2015/0174338 A1    Jun. 25, 2015

Related U.S. Application Data

(63) Continuation of application No. PCT/JP2013/057421, filed on Mar. 15, 2013.

(51) Int. Cl.
*A61M 5/32* (2006.01)
*A61M 5/28* (2006.01)
(Continued)

(52) U.S. Cl.
CPC .......... *A61M 5/3202* (2013.01); *A61M 5/003* (2013.01); *A61M 5/28* (2013.01);
(Continued)

(58) Field of Classification Search
CPC .............. A61M 5/3202; A61M 5/3213; A61M 2005/3109
(Continued)

(56) References Cited

U.S. PATENT DOCUMENTS 4,252,118 A * 2/1981 Richard .................. A61M 5/31
604/110
5,590,778 A * 1/1997 Dutchik ................. B65D 77/04
206/439
(Continued)

FOREIGN PATENT DOCUMENTS

JP    2004-513707 A    5/2004
JP    2010-534546       11/2010
(Continued)

OTHER PUBLICATIONS

International Search Report in PCT/JP2013/057421 dated May 28, 2013.

*Primary Examiner* — Gerald Landry, II
(74) *Attorney, Agent, or Firm* — Foley & Lardner LLP

(57) ABSTRACT

A syringe assembly includes a barrel including a barrel body portion, a cylindrical barrel end portion disposed at a distal end of the barrel body portion, the cylindrical barrel end portion including an annular head portion and an annular recessed portion, and a puncture needle having a puncture needle tip and having a proximal end fixedly inserted into the barrel end portion; and a seal cap mounted to the barrel, the seal cap including a closed distal end portion, an open proximal end portion, a hollow portion including (i) a barrel end storage portion, the barrel end storage portion being configured to store the barrel end portion, and (ii) a puncture needle storage portion extending from a distal end of the barrel end storage portion, an insertion portion configured to receive the puncture needle tip, and a projection portion formed on an inner surface of the barrel end storage portion.

19 Claims, 13 Drawing Sheets

(51) Int. Cl.
*B65D 25/10* (2006.01)
*B65D 47/32* (2006.01)
*B65D 53/00* (2006.01)
*B65D 81/20* (2006.01)
*A61M 5/00* (2006.01)
*A61M 5/31* (2006.01)
*A61M 5/34* (2006.01)

(52) U.S. Cl.
CPC .......... *B65D 25/108* (2013.01); *B65D 47/32* (2013.01); *B65D 53/00* (2013.01); *B65D 81/2069* (2013.01); *A61M 5/002* (2013.01); *A61M 5/3134* (2013.01); *A61M 5/343* (2013.01); *A61M 5/349* (2013.01); *A61M 2005/3109* (2013.01); *A61M 2205/19* (2013.01); *A61M 2209/06* (2013.01)

(58) Field of Classification Search
USPC ................ 604/162, 164.08, 192, 198, 263
See application file for complete search history.

(56) References Cited

U.S. PATENT DOCUMENTS

| | | | | |
|---|---|---|---|---|
| 5,980,495 | A * | 11/1999 | Heinz | A61M 5/3202 128/919 |
| 6,331,174 | B1 * | 12/2001 | Reinhard | A61M 5/28 427/2.3 |
| 6,551,286 | B1 * | 4/2003 | Claessens | A61M 5/3202 128/919 |
| 7,320,683 | B2 * | 1/2008 | Prais | A61M 5/3202 604/274 |
| 7,387,617 | B2 * | 6/2008 | Wittland | A61L 2/20 604/199 |
| 8,056,719 | B2 | 11/2011 | Porret et al. | |
| 2002/0045858 | A1 * | 4/2002 | Alchas | A61M 5/3129 604/117 |
| 2002/0062108 | A1 * | 5/2002 | Courteix | A61M 5/3202 604/198 |
| 2004/0030294 | A1 * | 2/2004 | Mahurkar | A61M 5/3232 604/192 |
| 2004/0049162 | A1 * | 3/2004 | Fisher | A61M 5/34 604/240 |
| 2005/0075611 | A1 * | 4/2005 | Hetzler | A61L 2/0011 604/192 |
| 2010/0198163 | A1 * | 8/2010 | Bonnet | A61M 5/3202 604/192 |
| 2010/0305511 | A1 | 12/2010 | Thibault et al. | |
| 2013/0012886 | A1 * | 1/2013 | Kawachi | A61M 5/3202 604/192 |
| 2015/0190566 | A1 * | 7/2015 | Okihara | A61M 5/002 206/365 |

FOREIGN PATENT DOCUMENTS

| | | |
|---|---|---|
| JP | 2012-254102 | 12/2012 |
| WO | WO-2011/114917 | 9/2011 |

* cited by examiner

SYRINGE ASSEMBLY, SYRINGE ASSEMBLY PACKAGE BODY, AND PRE-FILLED SYRINGE

CROSS-REFERENCE TO RELATED APPLICATIONS

This application is a continuation application filed under 35 U.S.C. 111(a) claiming the benefit under 35 U.S.C. §§ 120 and 365(c) of PCT International Application No. PCT/JP2013/057421 filed on Mar. 15, 2013, the entire contents of which is hereby incorporated by reference in its entirety

BACKGROUND

Technical Field

The present disclosure relates to a syringe assembly mounted with a seal cap, a prefilled syringe using the syringe assembly mounted with the seal cap, and a package body storing a plurality of syringe assemblies.

Background Art

A syringe having a puncture needle fixed at a distal end of a barrel is used as a syringe for administering a low dose of medical solution, such as an insulin syringe. When a pre-filled syringe in which a medical solution is prefilled is provided using a syringe of this type, the tip of the needle needs to be sealed. Such a seal cap for sealing the tip of a needle is disclosed, for example, in Japanese Unexamined Patent Application Publication (Translation of PCT Application) No. 2010-534546, or WO2011114917 (US2013012886).

A seal cap (shield 10) of JP 2010-534546 is configured to cover the distal tip of a syringe (partially shown on FIG. 2 of JP 2010-534546). The distal tip of the syringe 3 includes a hub 2 on which a needle 6 is fixed. The shield 10 has an open proximal end 11, a closed distal end 12, and a wall 13 extending from the proximal end 11 to the closed distal end 12. The internal face 14 of the wall 13 defines a cavity 15 for receiving the part of the distal tip of the syringe 3. A portion 14a of the internal face 14 is configured to be in contact with the hub 2 of the distal tip of the syringe 3 when the shield 10 is secured on the distal end tip of the syringe in order to protect the distal tip, for example during transport of an administration device before use.

In FIG. 3 of JP 2010-534546, the portion 14a of the internal face 14 of the wall 13 includes a plurality of grooves 16. The grooves 16 are regularly disposed along the circumference of the portion 14a, they are parallel to the longitudinal axes A of the shield 10. They allow air to flow during the assembly of the shield on the hub 2. A sticky surface of the shield is small, so the assembly is facilitated, and it is easy to have the respective longitudinal axis A and B (see JP 2010-534546 FIG. 2) of both the shield 10 and the administration device 3 remain confounded. The shield 10 of the device is therefore perfectly and accurately secured on the tip of the administration device 3. Because of the grooves created by the specific roughness of the portion 14a of the internal face 14 of the wall 13, it is then easier to remove the shield 10 from the tip of the administration device 3 at the time of use of the administration device 3.

In a syringe needle cap 10 of WO2011114917 (US2013012886), the cap is fitted to the tip of a barrel 21 of a prefilled syringe 20, and the tip of a syringe needle 22 is stuck into a needlepoint receiving section 12A on an inner layer portion 12 of the syringe needle cap 10. The outer circumference of a head section 21B on the tip of the prefilled syringe 20 is closely attached to a joining section 12B on the inner layer portion 12 of the syringe needle cap 10, thereby securely sealing the inner space within the syringe needle cap 10 which covers the syringe needle 22. An outer layer portion 11 functioning as the cap main body of the syringe needle cap 10 is formed from a transparent resin, and the inner layer portion 12 is formed from a transparent elastomer as the interior material. As a consequence, the entire syringe needle 22 of the prefilled syringe 20, including the tip section, can be seen from the outside.

In JP 2010-534546, the internal face of the opening of the seal cap (shield 10) has the plurality of grooves axially extending, and the seal cap is readily mounted to and removed from a barrel. However, since the seal cap is readily removed, when the barrel or the prefilled syringe mounted with the shield 10 is manufactured, and when the barrel or the prefilled syringe mounted with the shield 10 is transported, the shield 10 is likely to be removed unexpectedly from the barrel.

The syringe needle cap 10 of WO2011114917 (US2013012886) is configured such that a projection portion on an inner surface of a cap (ring shaped bump 12C) engages only with a ring shaped recessed portion at a barrel end portion (upper circumference of the head section 21B). Therefore, when a pressure difference is generated between the inside and the outside of the cap due to autoclave sterilization or the like, a force larger than an engagement force between the projection portion and the ring shaped recessed portion is likely to be applied to remove the cap.

When a syringe assembly is for example washed, air around the syringe assembly is sucked for removing foreign bodies, and sometimes pressure around the cap is reduced and pressure in the cap is relatively increased. Further, when the syringe assembly is sterilized by a sterilization method using a sterilization gas, such as, autoclave sterilization, ethylene oxide gas sterilization, or hydrogen peroxide gas sterilization, the inside of a sterilization apparatus in which the syringe assembly is put needs to be depressurized before the sterilization gas is introduced into the sterilization apparatus. Therefore, pressure around the cap is reduced and the pressure in the cap is relatively increased. Further, in the autoclave sterilization or the ethylene oxide gas sterilization, it is also considered that pressure in the sterilization apparatus is changed due to variation in air volume caused by temperature change, and pressure in the cap is increased relative to pressure around the cap. As described above, when the pressure in the cap is increased relative to the pressure around the cap, a repulsive force acts between the cap and the distal end of the barrel in a direction to separate the cap and the barrel. The repulsive force facilitates the removal of the cap from the distal end of the barrel.

SUMMARY OF INVENTION

In light of the forgoing, one objective of certain embodiments of the present invention is to provide a seal syringe assembly having a seal cap and a barrel without the unexpected removal of the seal cap from the barrel, even when the pressure difference is generated inside and outside the cap during a process of manufacturing the barrel or a prefilled syringe mounted with the seal cap, and during transportation of the barrel or the prefilled syringe mounted with the seal cap, a prefilled syringe using the seal syringe assembly, and a package body storing a plurality of syringe assemblies.

According to one embodiment, a syringe assembly includes a barrel including a barrel body portion, a cylindrical barrel end portion provided at a distal end of the barrel body portion, an annular head portion and an annular recessed portion formed at a proximal end of the annular head portion, and a puncture needle having a puncture needle tip at a distal end, and having a proximal end fixedly inserted into the barrel end portion, and a seal cap mounted to the barrel. The seal cap includes a closed distal end portion, an open proximal end portion, a hollow portion having a barrel end storage portion positioned distally from the open proximal end portion and storing the barrel end portion, and a puncture needle storage portion extending from a distal end of the barrel end storage portion and storing the puncture needle, an insertion allowing portion for receiving the insertion of the puncture needle tip of the puncture needle stored in the puncture needle storage portion, and a projection portion formed on the inner surface of the barrel end storage portion. The projection portion has a top portion, and a distal inclined portion extending distally from the top portion and having a projection height reduced distally. In the syringe assembly, the barrel end portion of the barrel is mounted with the seal cap, the puncture needle tip is inserted into the insertion allowing portion of the seal cap, the projection portion of the seal cap and the annular recessed portion of the barrel end portion are engaged with each other, and the distal inclined portion is hermetically pressed against the outer surface of the annular head portion.

According to another embodiment, a prefilled syringe includes the syringe assembly, a gasket stored and slidably moveable in the barrel in a liquid-tight manner, and a medical solution filled in a space formed by the barrel and the gasket.

According to another embodiment, a syringe assembly package body storing the syringe assembly includes a container body having an upper opening and having shape retainability, a barrel holder configured to hold a plurality of the syringe assemblies, the plurality of the syringe assemblies held by the barrel holder, and a releasable sheet-shaped lid member configured to hermetically seal the upper opening of the container body. The package body further includes a ventilation portion provided in the container body or the lid member, and having bacterial impermeability and a sterilization gas circulation property. The package body is configured to be subjected to high-pressure steam sterilization or ethylene oxide gas sterilization.

DETAILED DESCRIPTION

Figure 1:
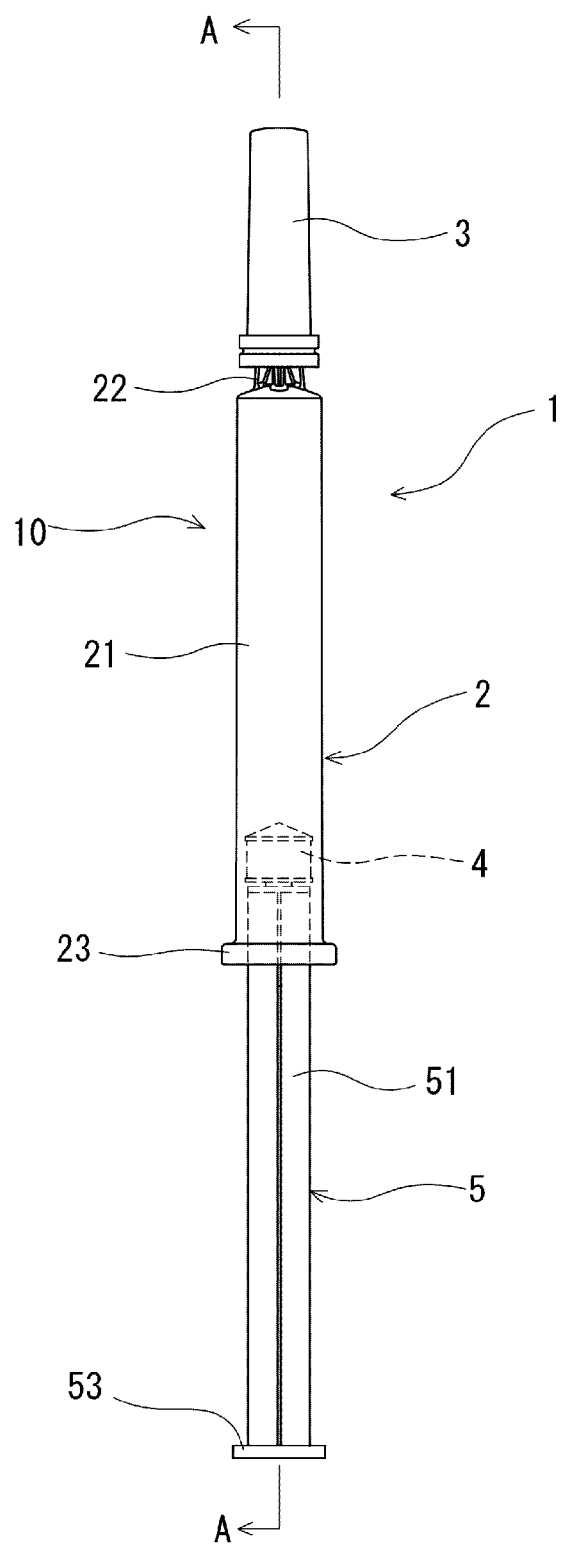
FIG. 1 is a front view of a prefilled syringe according to an embodiment of the present invention.

A seal syringe assembly according to an embodiment of the present invention and a prefilled syringe using the seal syringe assembly will be described according to an embodiment using the drawings.

The prefilled syringe 1 according to the embodiment of the present invention includes a syringe assembly (i.e., a barrel with a puncture needle mounted with a cap) 10, a gasket 4, and a medical solution 8. The gasket 4 is stored in the syringe assembly 10 and slidably moved in the syringe assembly 10 in a liquid-tight manner. The medical solution 8 is filled in a space formed by the syringe assembly 10 and the gasket 4.

The syringe assembly 10 according to the embodiment of the present invention includes a barrel 2, and a seal cap 3 mounted to the barrel 2.

The barrel 2 includes a barrel body portion 21, a cylindrical (hollow) barrel end portion (i.e., puncture needle mounting portion) 22, and the puncture needle 6. The barrel end portion 22 is provided at a distal end of the barrel body portion 21 and has an annular head portion 24 and an annular recessed portion 25 formed at a proximal end of the annular head portion 24. The puncture needle 6 has a puncture needle tip 61 at a distal end, and has a proximal end fixedly inserted into the barrel end portion 22.

The seal cap 3 according to the embodiment of the present invention includes a closed distal end portion 31, an open proximal end portion 32, a hollow portion 30, and a projection portion 36. The hollow portion 30 includes a barrel end storage portion 35 positioned distally from the open proximal end portion 32 and stores the barrel end portion 22, and a puncture needle storage portion 34 extending from a distal end of the barrel end storage portion 35. An insertion allowing portion 33 receives the insertion of the puncture needle tip 61 of the puncture needle 6 stored in the puncture needle storage portion 34. The projection portion 36 is formed on the inner surface of the barrel end storage portion 35. Further, the projection portion 36 has a top portion 36a, and a distal inclined portion 36b extending distally from the top portion 36a and having a projection height reduced distally.

In the syringe assembly 10, the barrel end portion 22 of the barrel 2 is mounted with the seal cap 3, the puncture needle tip 61 is inserted into the insertion allowing portion 33 of the seal cap 3, the projection portion 36 of the seal cap 3 and the annular recessed portion 25 of the barrel end portion 22 are engaged with each other, and the distal inclined portion 36b is hermetically pressed against the outer surface of the annular head portion 24.

Figure 2:
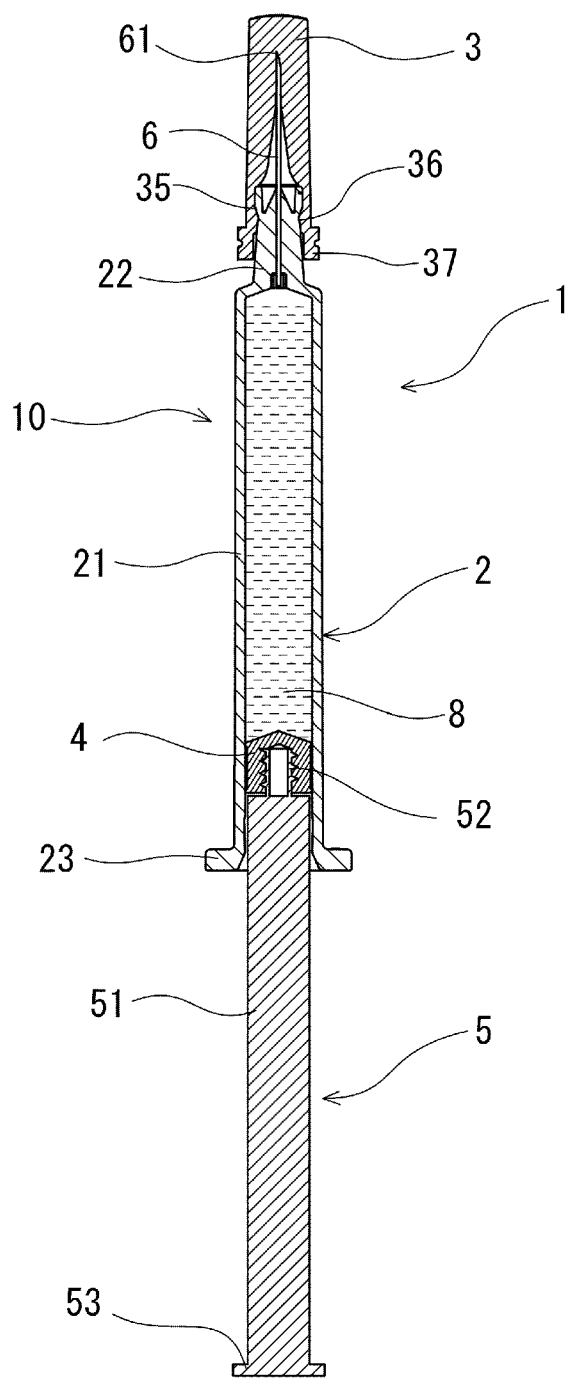
FIG. 2 is a cross-sectional view taken along line A-A of FIG. 1.

As illustrated in FIGS. 1 and 2, the prefilled syringe 1 includes the syringe assembly 10 including the barrel 2, and the seal cap 3 mounted to the barrel 2 to seal the needle tip of the puncture needle, the gasket 4 stored in the syringe assembly 10 and slidably moveable in the syringe assembly 10 in the liquid-tight manner, the medical solution 8 filled in the space formed by the syringe assembly 10 and the gasket 4, and a plunger 5 having been mounted to the gasket 4 or to be mounted to the gasket 4 when used.

The medical solution 8 is filled in the space formed by the barrel 2, the gasket 4, and the inside of the seal cap 3.

The medical solution 8 to be filled may include any medical solution, for example, a high concentration sodium chloride injection solution, minerals, a heparin sodium solution, nitroglycerin, an isosorbide dinitrate, a cyclosporine, a benzodiazepine, an antibiotic, a vitamin preparation (multi vitamin preparation), various amino acids, an antithrombotic drug such as heparin, insulin, antitumor drug, an analgesic, a cardiotonic, an intravenous anesthetic, an antiparkinsonism drug, a tumor therapeutic drug, an adrenal corticosteroid, a drug for irregular heartbeat, a correction electrolyte, an antiviral drug, or an immunostimulant.

The barrel 2 includes the barrel body portion 21, the cylindrical (hollow) barrel end portion 22 provided at the distal end of the barrel body portion 21, a flange 23 provided at a proximal end of the barrel body portion 21, and a puncture needle 6 having the proximal end fixedly inserted into the barrel end portion 22. The puncture needle 6 has the puncture needle tip 61 at the distal end. The proximal end of the puncture needle 6 is fixedly inserted into the hollow portion of the barrel end portion 22, and the inside of the puncture needle 6 communicates with an inner space 20 of the barrel 2. It is noted that the puncture needle 6 may be inserted into the hollow portion of the barrel end portion 22 of the barrel 2 previously molded and may be fixed to the barrel end portion 22 with an adhesive, by thermal welding, or the like. Meanwhile, the puncture needle 6 may be fixed to the barrel 2 by insert molding. In the insert molding, when the barrel 2 is molded, the barrel end portion 22 is formed into the cylindrical shape (hollow shape) into which the puncture needle 6 is inserted, and the proximal end of the puncture needle 6 is fixedly inserted into the hollow portion of the barrel end portion 22.

Figure 7:
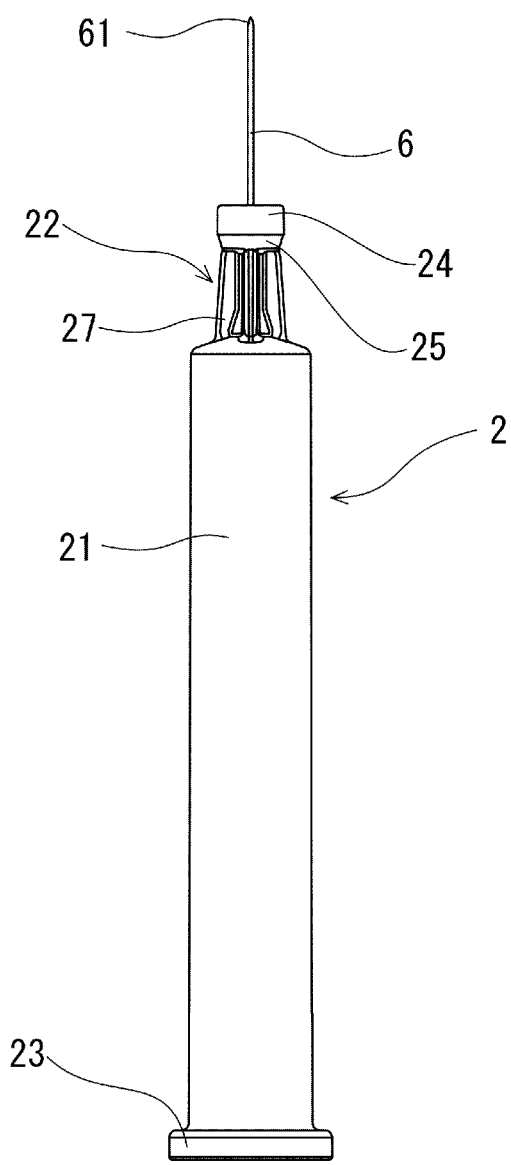
FIG. 7 is a front view of a barrel used for the prefilled syringe of FIGS. 1 and 2 and the syringe assembly of FIG. 3.
Figure 8:
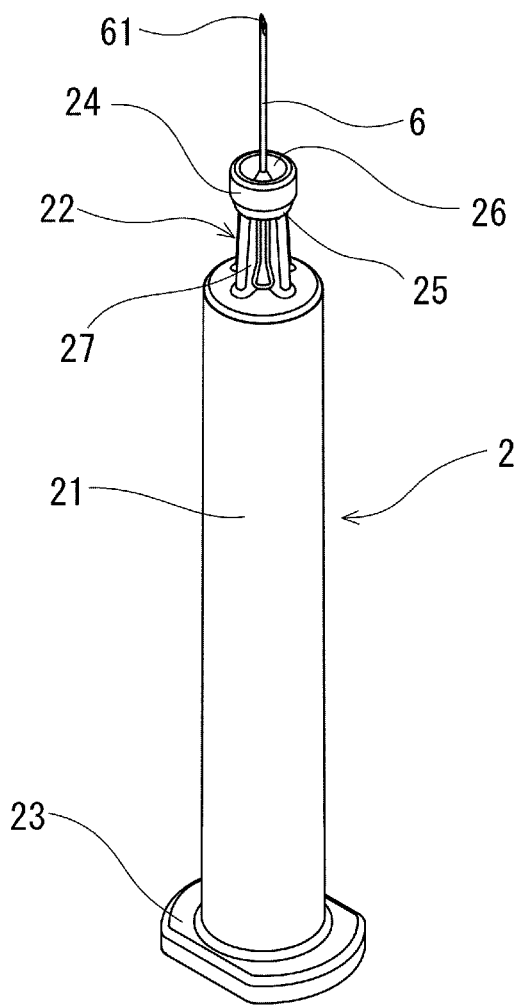
FIG. 8 is a perspective view of the barrel of FIG. 7.

The barrel 2 is transparent or translucent. The barrel body portion 21 is a substantially cylindrical portion storing the gasket 4 to be slidably moved in the liquid-tight manner. The barrel end portion 22 projects forward from the distal end (shoulder portion) of the barrel body portion, and has a hollow cylindrical shape having a diameter smaller than that of the barrel body portion. As illustrated in FIGS. 7 and 8, the barrel end portion 22 includes the annular head portion 24 provided at the distal end, a short tapered reduced diameter portion 25 provided at the proximal end of the annular head portion 24 and having a diameter reduced proximally, and a connection portion 27 configured to connect a proximal end of the tapered reduced diameter portion 25 and the distal end of the barrel body portion 21. The annular recessed portion is formed by the tapered reduced diameter portion 25. The annular head portion 24 is formed with a recess 26 recessed proximally from a distal end surface and a hollow conical portion positioned in the recess 26 and having a top on the distal end side. The connection portion 27 has an outer surface formed with a plurality of grooves extending in an axial direction of the barrel 2. The annular recessed portion may have not the tapered shape but a shape having a diameter only reduced to form a step between the annular recessed portion and the proximal end of the annular head portion 24. The connection portion 27 may be omitted to directly connect the proximal end of the annular recessed portion (tapered reduced diameter portion 25) and the distal end of the barrel body portion 21. The annular head portion 24 may have a hollow columnar shape (cylindrical shape) from which the recess 26 and the conical portion are omitted.

A material of the barrel 2 includes a resin, for example, a polypropylene, a polyethylene, a polystyrene, a polyamide, a polycarbonate, a polyvinyl chloride, poly(4-methyl pentene-1), an acrylic resin, an acrylonitrile-butadiene-styrene copolymer, polyester such as a polyethylene terephthalate, a cyclic olefin polymer, or a cyclic olefin copolymer. However, in particular, a resin such as polypropylene, cyclic olefin polymer, or cyclic olefin copolymer is preferably selected because such a resin is readily molded and has heat resistance.

The puncture needle 6 is employed which is hollow and has the puncture needle tip 61 at the distal end. A material of the puncture needle 6 generally includes a metal. The metal preferably includes stainless steel.

As illustrated in FIGS. 1 and 2, the gasket 4 includes a main body portion extending to have substantially the same outer diameter, and a plurality of annular ribs provided at the main body portion (two ribs are employed in the present embodiment, however, when two or more ribs are desired, an appropriate number of ribs may be employed as long as liquid tightness and slidability are satisfied). The ribs make liquid-tight contact with the inner surface of the barrel 2. A distal end surface of the gasket 4 has a shape corresponding to the shape of an inner surface of the distal end of the barrel 2 so that a gap is not formed between the gasket and the barrel as much as possible, when the distal end surface of the gasket abuts on the inner surface of the distal end of the barrel 2.

A material of the gasket 4 preferably includes elastic rubber (e.g., isoprene rubber, butyl rubber, latex rubber, silicone rubber), a synthetic resin (e.g., a styrenic elastomer such as SBS elastomer or SEBS elastomer, or an olefinic elastomer such as ethylene-α-olefin copolymer elastomer), or the like.

The gasket 4 is provided with a recessed portion extending inward from a proximal end of the gasket. The recessed portion is formed as an internal thread to be threadedly engaged with an external thread portion formed on the outer surface of a projection portion 52 formed at a distal end of the plunger 5. The internal and external threads are threadedly engaged, so that the plunger 5 is not removed from the gasket 4. The plunger 5 may be separated usually, and mounted when used. The plunger 5 includes the projection portion 52 projecting forward cylindrically from a disk portion at the distal end, and the outer surface of the projection portion is formed with the external thread threadedly engaged with the recessed portion of the gasket 4. Further, the plunger 5 includes a main body portion 51 having a cross-shaped cross section and extending axially, and a pressure disk portion 53 provided at a proximal end.

The seal cap 3 for the barrel according to the embodiment of the present invention is used by being mounted to the barrel including the barrel body portion 21, the cylindrical barrel end portion 22 provided at the distal end of the barrel body portion 21 and having the annular head portion 24 and the annular recessed portion 25 formed at the proximal end of the annular head portion 24, and the puncture needle 6 having the puncture needle tip 61 at the distal end and having the proximal end fixedly inserted into the barrel end portion 22.

The seal cap 3 includes the closed distal end portion 31, the open proximal end portion 32, the hollow portion 30 having a barrel end storage portion 35 configured to store the barrel end portion 22 and a puncture needle storage portion 34 extending from the barrel end storage portion 35, the insertion allowing portion 33 configured to receive the insertion of the puncture needle tip 61 of the puncture needle 6 stored in the puncture needle storage portion 34, and the projection portion 36 formed on the inner surface of the barrel end storage portion 35. When the seal cap 3 is mounted to the barrel end portion 22 of the barrel 2, the puncture needle tip 61 is inserted and sealed in the insertion allowing portion 33 of the seal cap 3, the projection portion 36 and the annular recessed portion 25 of the barrel end portion 22 of the barrel 2 are engaged with each other, and the distal inclined portion 36b is hermetically pressed against the outer surface of the annular head portion 24.

Since the seal cap has such a projection portion 36, when the pressure difference is generated inside and outside the seal cap 3, specifically, when the pressure in the seal cap 3 is increased relative to the pressure outside the seal cap 3, an engagement force between the projection portion, and the annular head portion and the annular recessed portion prevents the removal of the seal cap 3 from the barrel 2.

Specifically, the seal cap 3 includes the projection portion 36 provided on the inner surface positioned distally by a predetermined length from the open proximal end portion 32. The projection portion 36 has the top portion 36a projecting most, and the inclined portion (tapered portion) 36b extending toward an opening from the top portion 36a, and having a projection height gradually reduced distally. In particular, in the present embodiment, the projection portion 36 is formed as an annular projection portion, and the inclined portion 36b is formed as a tapered portion in which the inner diameter of the barrel end storage portion 35 is reduced distally.

The inner diameter of the barrel end storage portion 35 at the top portion 36a is slightly smaller than the outer diameter at the distal end of the annular recessed portion 25 in the barrel end portion 22 of the barrel 2. Therefore, when the seal cap 3 is mounted to the barrel end portion 22 of the barrel 2, the projection portion 36 and the annular recessed portion 25 are engaged with each other. Further, while the seal cap 3 is mounted to the barrel end portion 22 of the barrel 2, the distal inclined portion 36b extends distally from the annular recessed portion 24. The inner diameter of the barrel end storage portion 35 at least in the vicinity of the proximal end of the distal inclined portion 36b is slightly smaller than the outer diameter of the annular head portion 24 in the barrel end portion 22 of the barrel 2. Therefore, when the seal cap 3 is mounted to the barrel end portion 22 of the barrel 2, the distal inclined portion 36b is hermetically pressed against the outer surface of the annular head portion 24, and unexpected removal of the seal cap 3 from the barrel 2 is further reduced.

It is noted that, in the seal cap 3 of the present embodiment, the inner diameter of the barrel end storage portion 35 at the distal end of the distal inclined portion 36b is slightly smaller than the outer diameter of the annular head portion 24 in the barrel end portion 22 of the barrel 2. Therefore, when the seal cap 3 is mounted to the barrel end portion 22 of the barrel 2, the whole inner surface of the distal inclined portion 36b is hermetically pressed against the outer surface of the annular head portion 24. Therefore, the distal inclined portion 36b hermetically pressed against the outer surface of the annular head portion 24 has an area increased, and the unexpected removal of the seal cap 3 from the barrel 2 is further reduced.

In the seal cap 3 of the present embodiment, the projection portion 36 is formed into an annular shape along the inner surface of the barrel end storage portion 35. Therefore, the distal inclined portion 36b hermetically pressed against the outer surface of the annular head portion 24 has an area increased, compared with the projection portion 36 intermittently formed on the inner surface of the barrel end storage portion 35, and the unexpected removal of the seal cap 3 from the barrel 2 is further reduced. The projection portion 36 may be formed intermittently on the inner surface of the barrel end storage portion 35.

Further, in the seal cap 3 of the present embodiment, the projection portion 36 has a proximal inclined portion 36c extending from the top portion 36a toward an opening end (proximal end), and having a projection height gradually reduced toward the opening end (proximal end). Therefore, when the seal cap 3 is mounted to the barrel end portion 22 of the barrel 2, the top portion 36a of the projection portion 36 readily overrides the annular head portion 24 of the barrel end portion 22 from the distal end side.

In particular, in the present embodiment, the projection portion 36 is formed as an annular projection portion, and the proximal inclined portion 36c is formed as a proximal tapered portion in which the inner diameter of the barrel end storage portion 35 is increased proximally. It is noted that, in the seal cap 3 of the present embodiment, the proximal inclined portion (proximal tapered portion) 36c has a length shorter than and a taper angle larger than the distal inclined portion (distal tapered portion) 36b.

Figure 6:
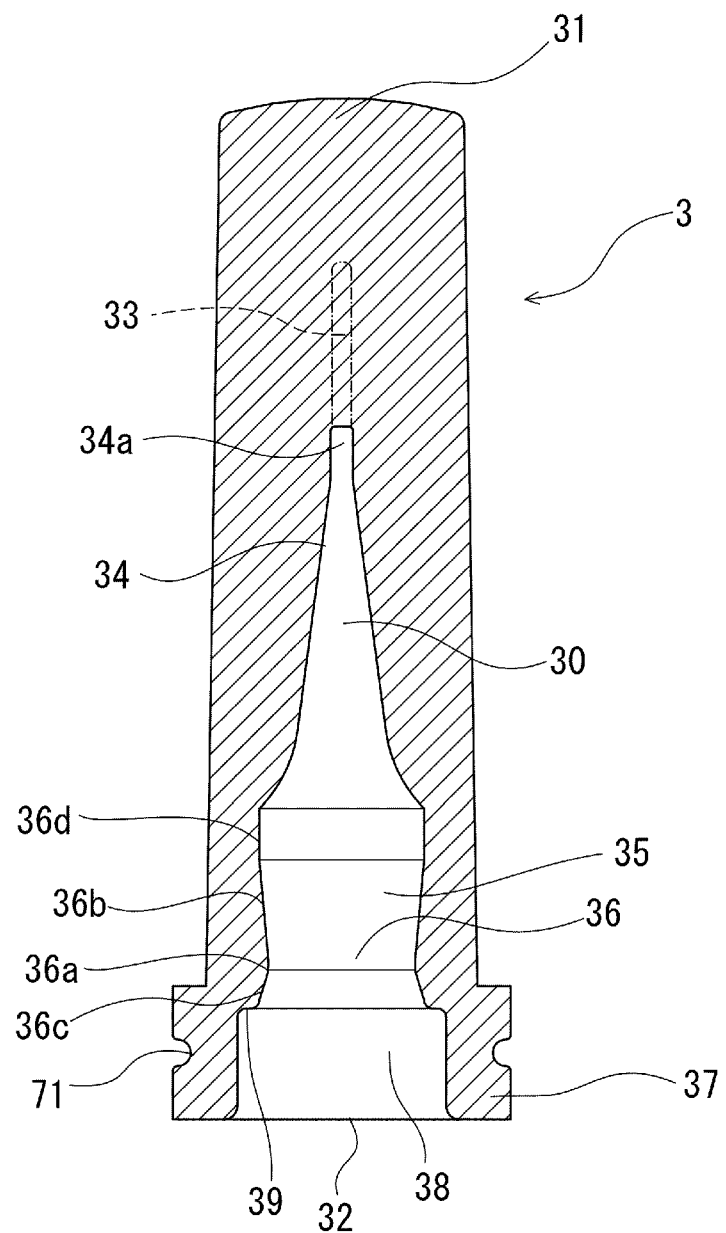
FIG. 6 is an enlarged cross-sectional view taken along line B-B of FIG. 4.
Figure 9:
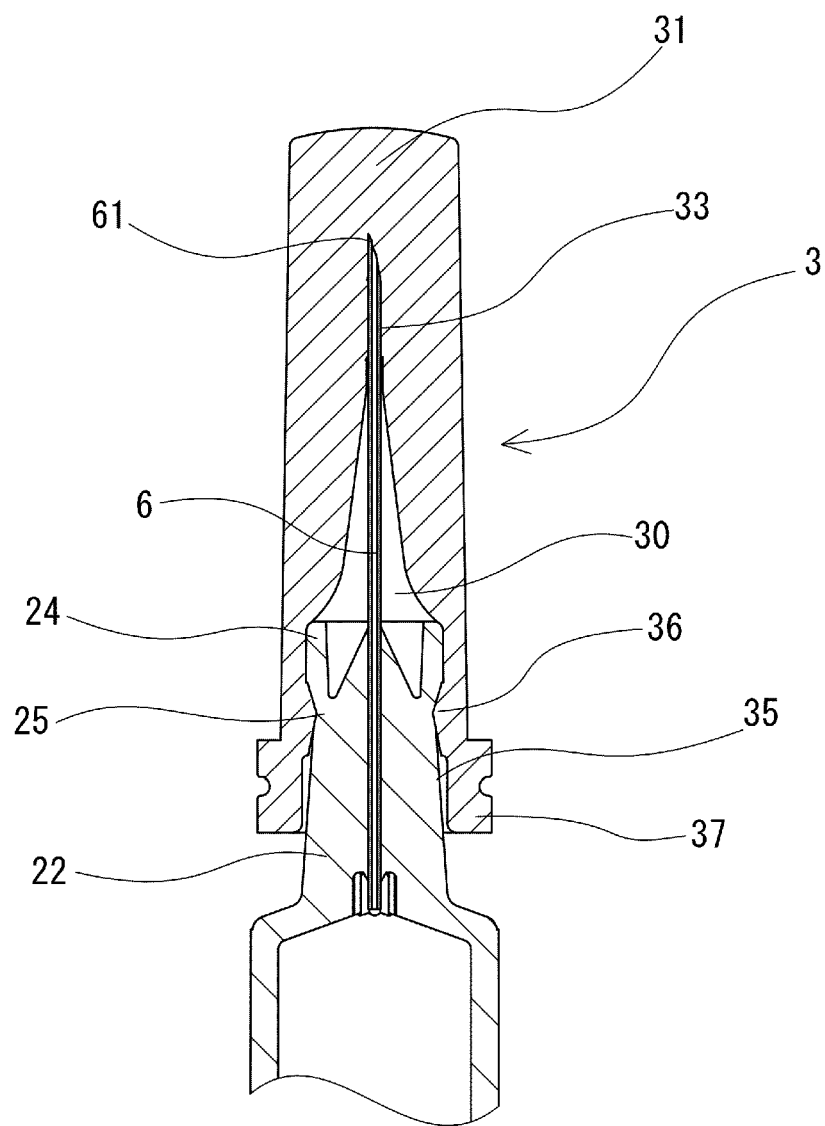
FIG. 9 is an enlarged cross-sectional view of a distal end of the syringe assembly of FIG. 3.

In the syringe 1 of the present embodiment, as illustrated in FIGS. 6 and 9, the inner surface of the barrel end storage portion 35, on the distal end side from the distal inclined portion 36b, is hermetically pressed against the outer surface of the annular head portion 24. Specifically, the barrel end storage portion 35 has a linear portion 36d extending distally from the distal end of the distal inclined portion 36b of the projection portion 36 by a predetermined length (specifically, to the proximal end of the puncture needle storage portion 34). In linear portion 36d, the inner diameter of the barrel end storage portion 35 is constant, and is slightly smaller than the outer diameter of the annular head portion 24 in the barrel end portion 22 of the barrel 2. Therefore, when the seal cap 3 is mounted to the barrel end portion 22 of the barrel 2, the linear portion 36d is hermetically pressed against the outer surface of the annular head portion 24. Therefore, airtightness in the hollow portion 30 of the seal cap 3 is securely maintained. In the linear portion 36d, the inner diameter of the barrel end storage portion 35 may be larger than the outer diameter of the annular head portion 24 in the barrel end portion 22 of the barrel 2. Further, the linear portion 36d may be omitted, and the distal inclined portion 36b may be extended to the proximal end of the puncture needle storage portion 34.

The seal cap 3 preferably has a removal resistance from the barrel 2 of 1.5 to 20 N, especially, 5 to 8 N. Therefore, while the unexpected removal of the seal cap 3 from the barrel 2 is prevented, the seal cap 3 can be readily removed from the barrel 2 when the prefilled syringe 1 is used.

The inclination angle (taper angle) of the distal inclined portion 36b in the projection portion 36 of the seal cap 3 is preferably 1 to 10°, especially, 1 to 6°. Further, the projection height of the top portion of the projection portion 36 is preferably 0.05 to 0.5 mm, especially, 0.1 to 0.25 mm.

In the present embodiment, the proximal end of the distal inclined portion 36b in the projection portion 36 of the seal cap 3 is positioned around the annular recessed portion 24 in the barrel end portion 22 of the barrel 2, and the inner diameter of the barrel end storage portion 35 at least in the vicinity of the proximal end of the distal inclined portion 36b is slightly smaller than the outer diameter of the annular recessed portion 24. Therefore, the distal inclined portion 36b of the projection portion 36 of the seal cap 3 is hermetically pressed against the outer surface of the annular recessed portion 25. Therefore, the unexpected removal of the seal cap 3 from the barrel 2 is further reduced.

Further, in the present embodiment, the annular recessed portion 25 includes the tapered reduced diameter portion provided at the proximal end of the annular head portion 24, and having a diameter reduced proximally. Therefore, when the seal cap 3 is removed from the barrel 2, the projection portion 36 of the seal cap 3 is pressed and opened outward along the annular recessed portion 25, and readily overrides the annular head portion 24.

In the seal cap 3, the distal inclined portion 36b of the projection portion 36 has a portion hermetically pressed against the outer surface of the annular head portion 24. The portion preferably has a length in the axial direction of the annular head portion 24 of 0.1 to 2.0 mm, especially, 0.3 to 1.5 mm. Therefore, the unexpected removal of the seal cap 3 from the barrel 2 is reduced, and the removal resistance of the seal cap 3 from the barrel 2 is inhibited from being increased more than necessary.

Figure 10:
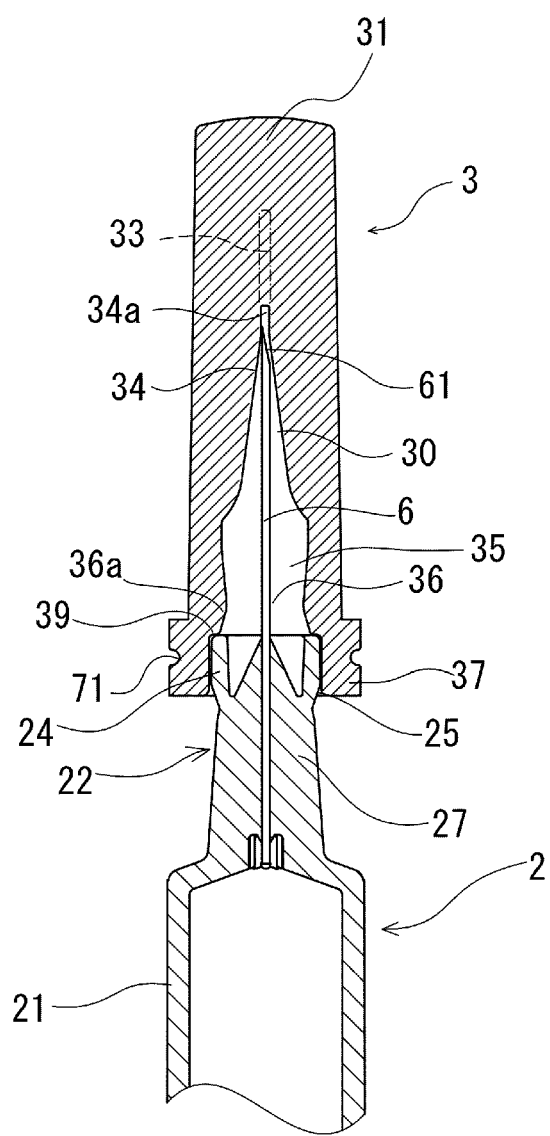
FIG. 10 is a schematic diagram illustrating the function of a syringe assembly according to an embodiment of the present invention.

Further, in the seal cap 3 of the present embodiment, the hollow portion 30 includes a barrel end introduction portion 38 formed from the open proximal end portion 32 of the seal cap 3 to the proximal end of the barrel end storage portion 35 (projection portion 36), and extending with substantially the same inner diameter. The barrel end introduction portion 38 has an inner diameter slightly larger than the maximum inner diameter of the barrel end storage portion 35, and the inner diameter is slightly larger than the outer diameter of the annular head portion 24 in the barrel end portion 22 of the barrel 2. Therefore, the barrel end introduction portion 38 serves as an introduction portion for the barrel end portion 22 when the seal cap 3 is mounted to the barrel end portion 22 of the barrel 2. Further, the barrel end introduction portion 38 has an annular rising surface 39 rising to be directed toward the open proximal end portion 32, on a boundary with the proximal end of the barrel end storage portion 35 (projection portion 36). Accordingly, when the distal end of the barrel 2 is inserted into the barrel end introduction portion 38 of the seal cap 3, the barrel end portion 22 of the barrel 2 enters the barrel end introduction portion 38, and then an annular distal end surface of the annular head portion 24 of the barrel end portion 22 abuts on the annular rising surface 39 as illustrated in FIG. 10. In this state, the puncture needle 6 is positioned substantially parallel with the axis of the seal cap 3, and is ready to enter a small diameter tip portion 34a of the puncture needle storage portion 34.

It is noted that, when at least the inner diameter of the proximal end is larger than the outer diameter of the annular head portion 24 in the barrel end portion 22 of the barrel 2, the barrel end introduction portion serves as an introduction portion for the barrel end portion 22. Therefore, the inner diameter of the barrel end introduction portion may be reduced distally, different from the above-mentioned embodiment. Further, the annular rising surface 39 may be omitted from the barrel end introduction portion, and the inner diameter of the barrel end introduction portion may be reduced toward the proximal end of the barrel end storage portion 35 (projection portion 36). Accordingly, when the annular distal end surface of the annular head portion 24 of the barrel end portion 22 enters up to the boundary between the proximal end of the barrel end storage portion 35 (projection portion 36) and the barrel end introduction portion, the puncture needle 6 is positioned substantially parallel with the axis of the seal cap 3, and enters the small diameter tip portion 34a of the puncture needle storage portion 34.

In the seal cap 3 of the present embodiment, the puncture needle storage portion 34 has a proximal end positioned at the distal end of the linear portion 36d of the barrel end storage portion 35, and has an inner diameter sharply reduced distally. Further, the proximal end of the puncture needle storage portion 34 is formed as a curved annular surface being curved inward to prevent the insertion of the puncture needle 6, and securely guide the puncture needle 6 distally. A main body portion (center part) of the puncture needle storage portion is formed as a tapered portion having a diameter reduced distally, and has a distal end formed with a small diameter tip portion 34a having an inner diameter slightly larger than the outer diameter of the puncture needle 6, and extending with substantially the same inner diameter.

As illustrated in FIG. 10, the seal cap is preferably configured such that, while the barrel end portion 22 of the barrel 2 is inserted into the seal cap, and the annular distal end surface of the annular head portion 24 of the barrel end portion 22 abuts on the annular rising surface 39 of the barrel end introduction portion 38 of the seal cap 3, the puncture needle tip 61 of the puncture needle 6 enters the small diameter tip portion 34a of the puncture needle storage portion 34, but does not reach the insertion allowing portion 33. The insertion allowing portion 33 is positioned forward (distally) from the barrel end introduction portion 38, to be precise forward from and on the extension of the small diameter tip portion 34a of the puncture needle storage portion 34. The shape of the puncture needle storage portion 34 is not particularly limited as long as the puncture needle 6 can be stored, and may be for example a mere cylinder.

Further, the proximal end of the seal cap 3 is formed with a flange 37 for gripping, projecting annularly outward, and the flange 37 is provided with an annular recessed portion 71. The distal end side of the flange 37 is positioned distally from the annular rising surface 39 of the hollow portion 30, and near the top portion 36a of the projection portion 36 (slightly on the proximal end opening portion 32 side from the top portion 36a, in FIG. 6).

For a material of the seal cap 3, at least the insertion allowing portion 33 needs to include an elastic material allowing the insertion of the puncture needle. The elastic material into which the puncture needle can be inserted preferably includes, for example, rubber such as butyl rubber, isoprene rubber, latex rubber, silicone rubber, or an elastomer such as a synthetic resin elastomer (e.g., a styrenic elastomer such as SBS elastomer or SEBS elastomer), or an olefinic elastomer such as ethylene-α-olefin copolymer elastomer.

In the seal cap 3 of the present embodiment, at least the barrel end storage portion 35 and the insertion allowing portion 33 (whole of the seal cap in the present embodiment) include the elastic material into which the puncture needle can be inserted. Therefore, when the seal cap 3 is mounted to the barrel end portion 22 of the barrel 2, the inner surface of the barrel end storage portion 35 is elastically deformed following the outer surface of the annular head portion 24 of the barrel end portion 22. Therefore, the inner surface of the barrel end storage portion 35 and the outer surface of the annular head portion 24 of the barrel end portion 22 are brought into closer contact with each other, and the unexpected removal of the seal cap 3 from the barrel 2 is further reduced. For the seal cap 3, only the insertion allowing portion 33 or the vicinity thereof may include the elastic material into which the puncture needle can be inserted, and the outside of the insertion allowing portion 33 may include a hard or semi-hard material.

A material of the outside portion of the seal cap includes, for example, a resin such as a polypropylene, a polyethylene, a polystyrene, a polyamide, a polycarbonate, a polyvinyl chloride, poly(4-methyl pentene-1), an acrylic resin, an acrylonitrile-butadiene-styrene copolymer, a polyester such as polyethylene terephthalate, or a cyclic polyolefin. Further, for the seal cap, at least the barrel end storage portion and the insertion allowing portion may include the elastic material into which the puncture needle can be inserted, and at least part of the outside thereof may be covered with a cover member including the hard or semi-hard material.

Figure 3:
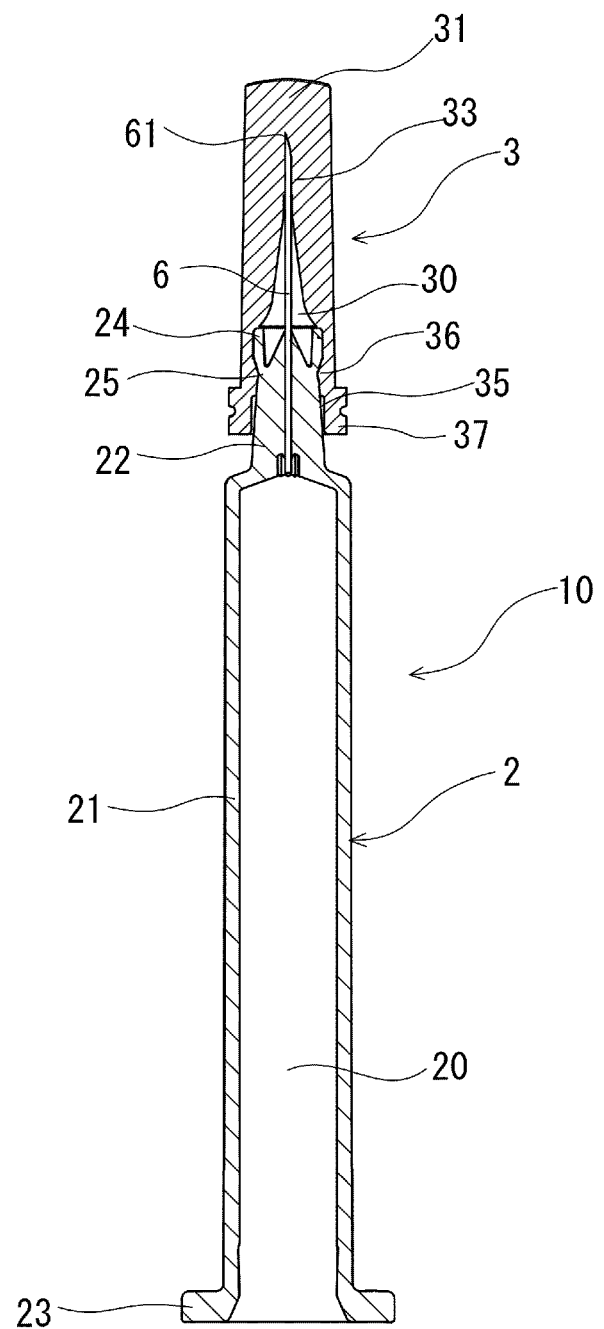
FIG. 3 is an enlarged cross-sectional view of a syringe assembly according to an embodiment of the present invention used for the prefilled syringe of FIGS. 1 and 2.
Figure 4:
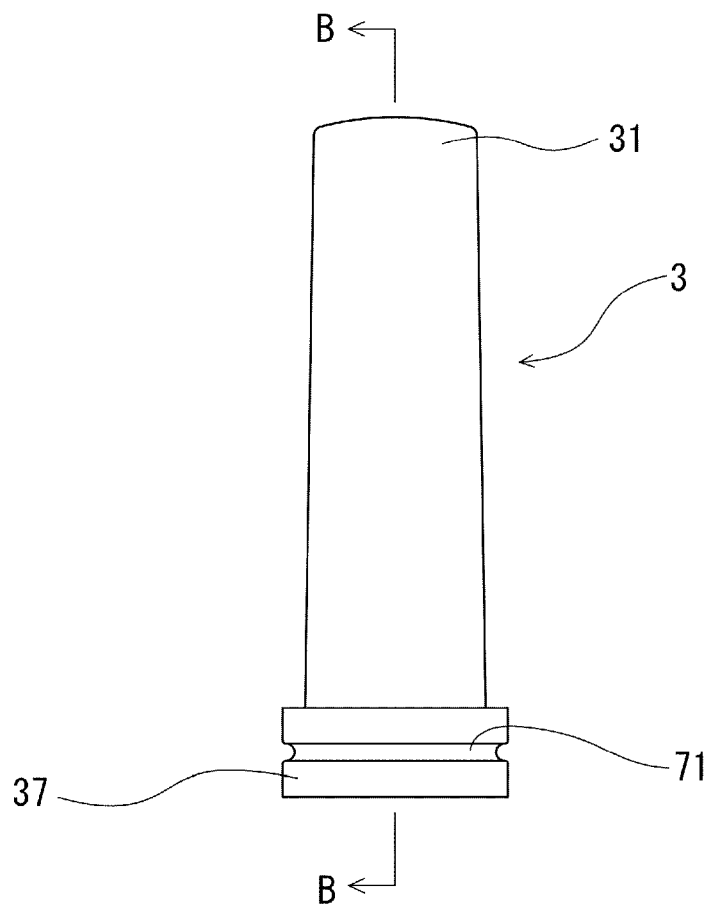
FIG. 4 is an enlarged front view of a barrel seal cap used for the prefilled syringe of FIGS. 1 and 2 and the syringe assembly of FIG. 3.
Figure 5:
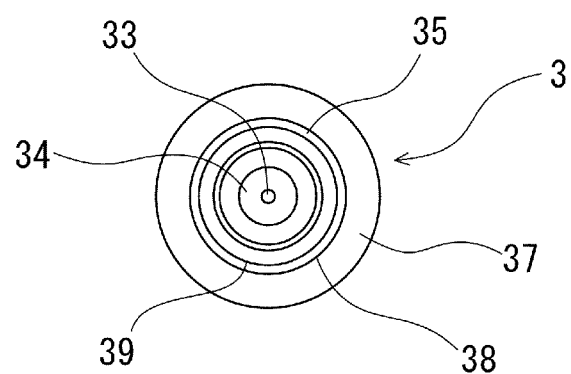
FIG. 5 is a bottom view of the barrel seal cap of FIG. 4.

In the syringe assembly 10 according to an embodiment of the present invention, as illustrated in FIG. 3, the seal cap 3 is mounted to the distal end (barrel end portion 22) of the barrel 2, the puncture needle tip 61 of the puncture needle 6 is inserted into the insertion allowing portion 33 of the seal cap 3 and sealed in the liquid-tight manner, the annular recessed portion 25 of the barrel end portion 22 and the projection portion 36 formed on the inner surface of the barrel end storage portion 35 are engaged with each other, and the distal inclined portion 36b is hermetically pressed against the outer surface of the annular head portion 24.

Next, a package body storing a plurality of the syringe assemblies will be described according to an embodiment of the present invention illustrated in the drawings, using FIGS. 11 to 15.

A sterilizable or sterilized prefilled syringe assembly package body 100 stores a plurality of the syringe assemblies according to the embodiment of the present invention. The prefilled syringe assembly package body 100 includes a container body 102, a barrel holder 104, the plurality of the syringe assemblies 10, and a sheet-shaped lid member 103. The container body 102 has a top opening and has shape retainability. The barrel holder 104 holds the plurality of the syringe assemblies 10 stored in the container body 102. The plurality of the syringe assemblies 10 is held by the barrel holder 104. The sheet-shaped lid member 103 releasably hermetically seals the upper opening of the container body 102.

The prefilled syringe assembly package body 100 according to the embodiment of the present invention employs a sterilizable or sterilized prefilled syringe assembly package body. A sterilization method includes high-pressure steam sterilization, radiation or electron beam sterilization, or ethylene oxide gas sterilization.

Figure 11:
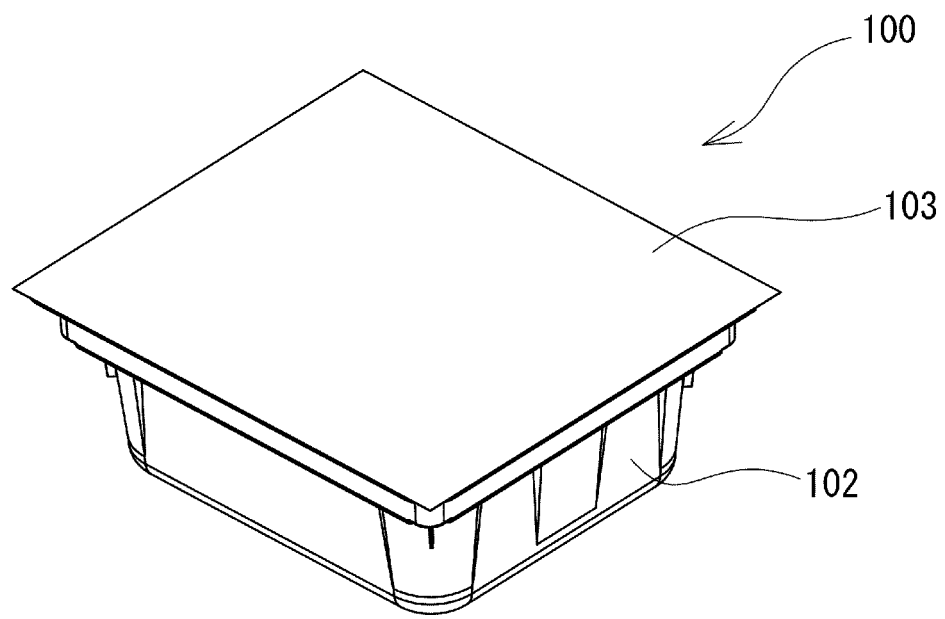
FIG. 11 is a perspective view of a syringe assembly package body according to an embodiment of the present invention.
Figure 12:
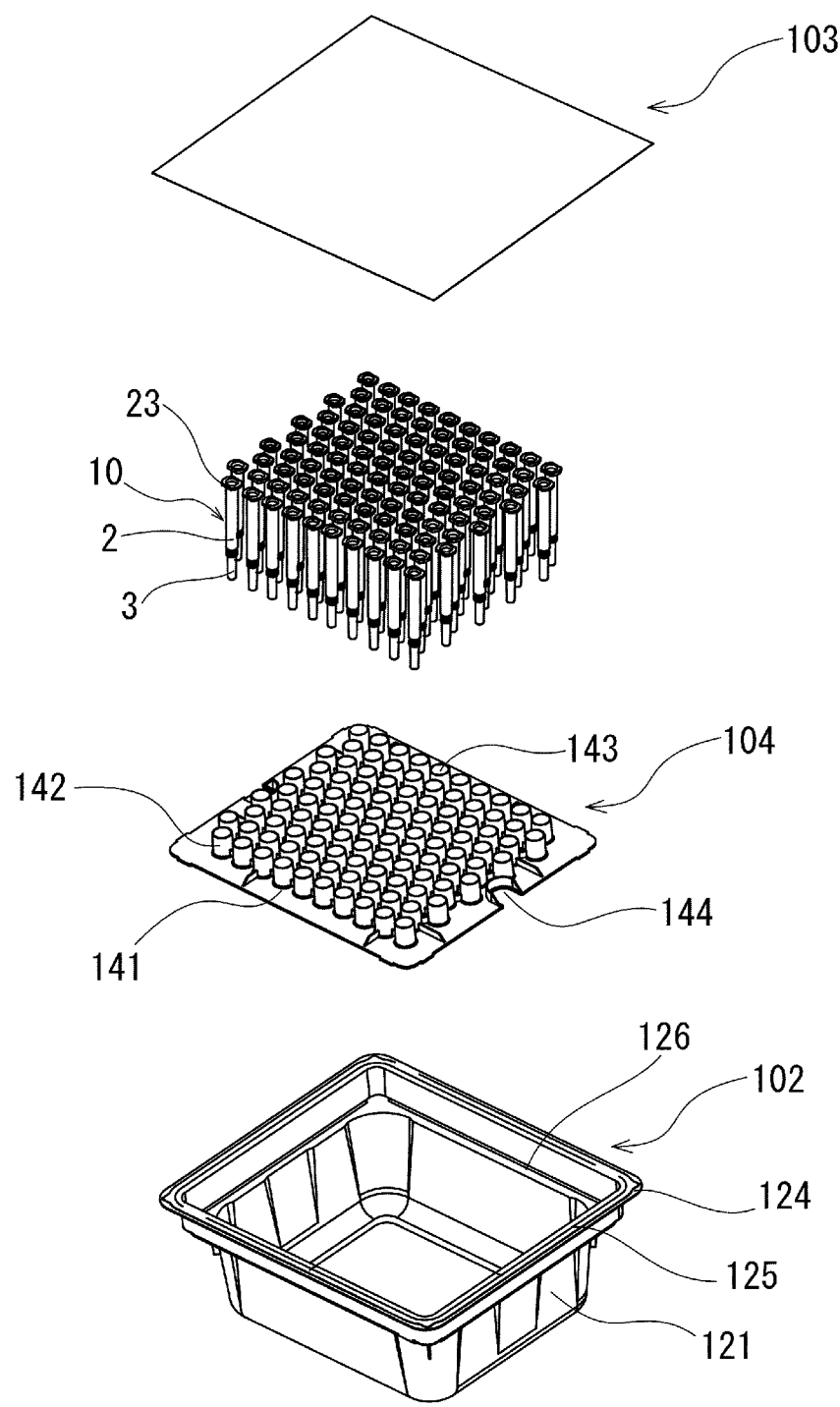
FIG. 12 is a schematic diagram illustrating an exploded view of the syringe assembly package body of FIG. 11.
Figure 13:
FIG. 13 is a front view of the syringe assembly package body of FIG. 11.
Figure 14:
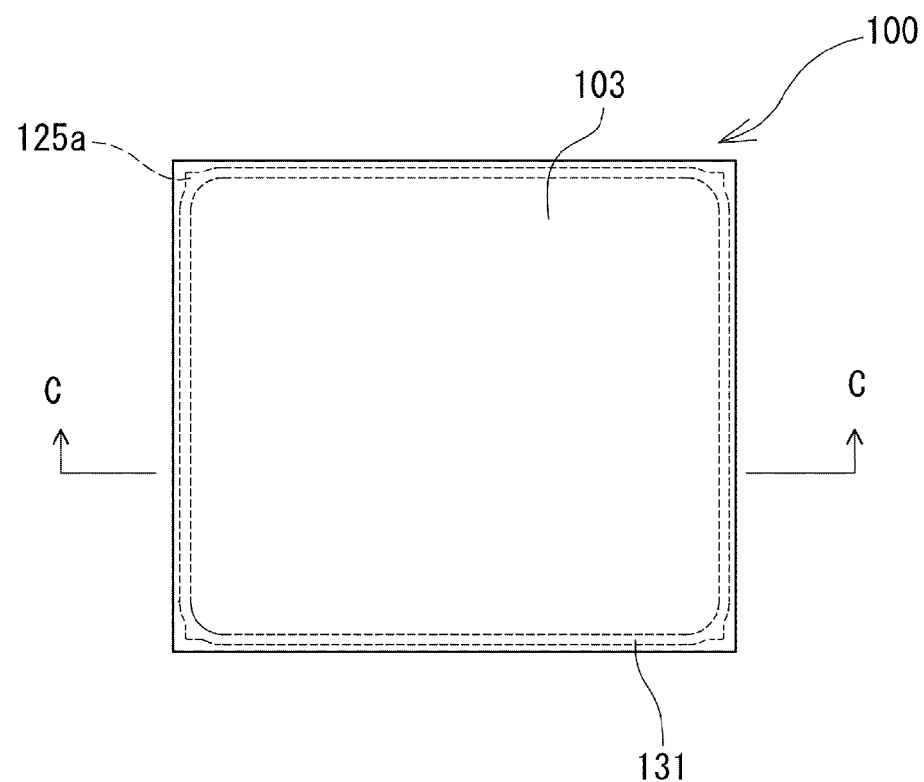
FIG. 14 is a plan view of the syringe assembly package body of FIG. 13.
Figure 15:
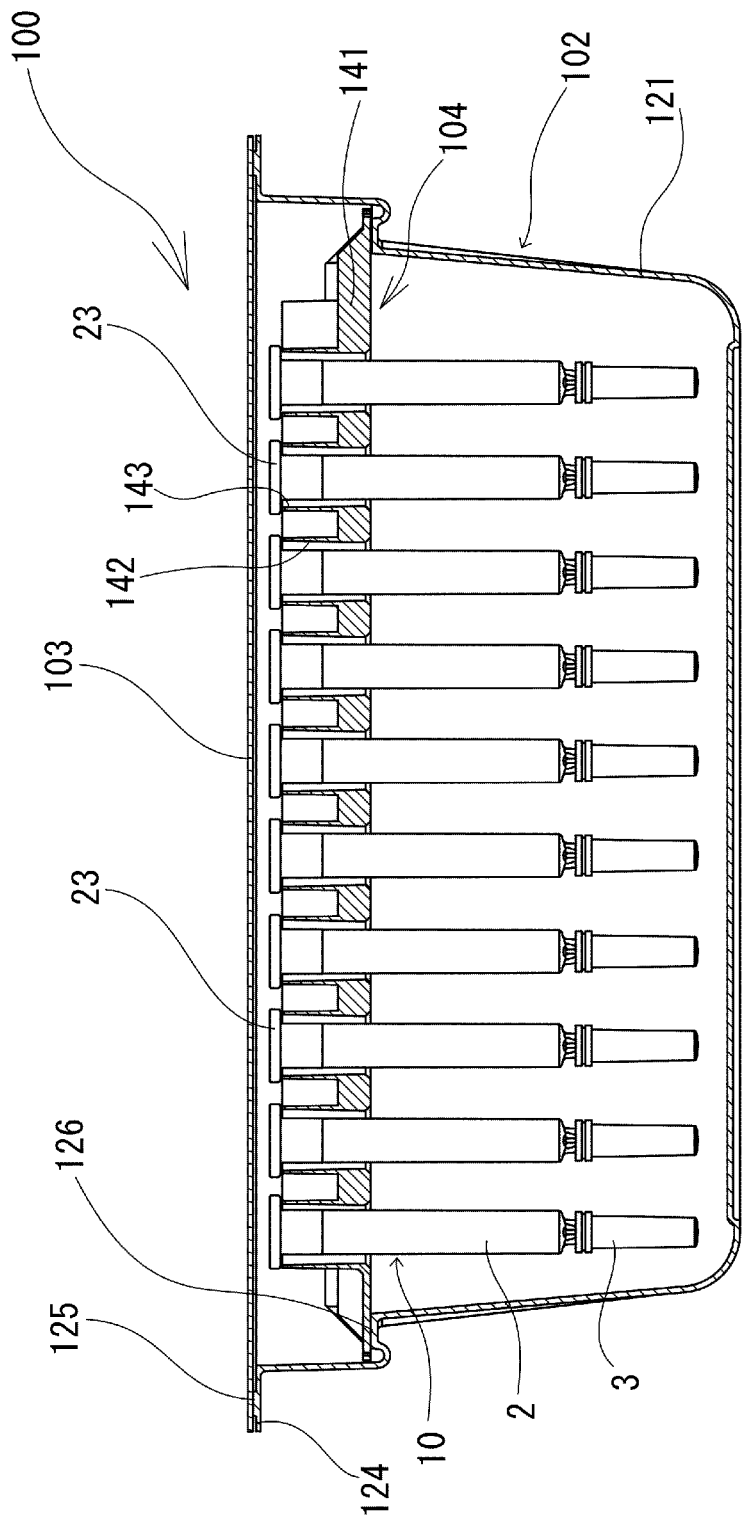
FIG. 15 is an enlarged cross-sectional view taken along line C-C of FIG. 14.

As illustrated in FIGS. 11, 12, and 15, the prefilled syringe assembly package body 100 according to the embodiment of the present invention includes the container body 102, the barrel holder 104 configured to hold the plurality of the syringe assemblies 10, the plurality of the syringe assemblies 10 held by the barrel holder 104, and the sheet-shaped lid member 103 configured to releasably hermetically seal the upper opening of the container body 102. Further, the package body 100 includes a ventilation portion provided in the container body 102 or the sheet-shaped lid member 103, and having bacterial impermeability and a sterilization gas circulation property.

As illustrated in FIGS. 11 to 15, the container body 102 is formed into a tray shape having a predetermined depth to have a certain level of strength and shape retainability. The container body 102 includes a main body portion 121, a barrel holder holding portion 126, and an annular flange 124.

The barrel holder holding portion 126 is formed at the upper part of the main body portion 121, and holds the peripheral edge of the barrel holder 104 holding the plurality of the syringe assemblies 10. The annular flange 124 is provided at the upper opening.

Further, the annular flange 124 has an upper surface provided with an annular heat-sealing protrusion 125 for fixing the sheet-shaped lid member 103. The barrel holder holding portion 126 is formed at a position located on the bottom surface side from the flange 124 by a predetermined length. In the container body 102 according to a first embodiment, the barrel holder holding portion 126 is formed as an annular stepped portion, and the peripheral edge of the barrel holder 104 holding the plurality of the syringe assemblies 10 can be mounted thereon.

The container body 102 preferably has a certain level of shape retainability and rigidity. Further, a thermoplastic material having heat resistance (120° C. or more) is preferably employed for high-pressure steam sterilization. A material having a certain level of shape retainability and rigidity, heat resistance, and thermal plasticity includes, for example, a polyolefin such as a polypropylene or a polyethylene, a vinyl chloride resin, a polystyrene/polypropylene resin, a polyethylene/ionomer resin (e.g., ethylene-based, styrene-based, fluorine-based)/polyethylene, a polyester resin (e.g., polyethylene terephthalate, polybutylene terephthalate, amorphous polyethylene terephthalate), or PP/EVOH/PP (laminate). In this case, the thickness of the container body 102 is preferably approximately 0.05 to 4.00 mm, especially, 1.00 to 2.00 mm.

Further, the container body 102 may be configured to be subjected to the radiation or electron beam sterilization, and preferably uses a so-called radiation-resistant material. The radiation-resistant material (e.g., radiation-resistant polyolefin) can be used which has radiation resistance obtained by adding a hindered amine, and further an antioxidant, nucleating agent, or the like to a polyolefin (e.g., a polypropylene, a polyethylene). An example of the hindered amine includes bis(2,2,6,6-tetramethyl-piperidyl)sebacate, bis(2,2,6,6-tetramethyl-piperidinyl)adipate, bis(2,2,6,6-tetramethyl-piperidyl)fumarate, or the like. The antioxidant includes 1,1,3-tris(2-methyl-hydroxy-5-t-butylphenyl)butane, tris(3,5-di-T-butyl-4-hydroxybenzyl)isocyanurate, tetrakis[methylene-3-(3,5-di-t-butyl-4-hydroxyphenyl)propionate]-methane, or the like. An example of the nucleating agent includes 1,3,2,4-dibenzylidenesorbitol, 1,3,2,4-di(p-methyl-benzylidene)sorbitol, or the like.

As illustrated in FIGS. 12 and 15, the barrel holder 104 configured to hold the plurality of the syringe assemblies 10 includes a substrate portion 141 and a plurality of cylindrical portions 142 projecting upward from the substrate portion 141. Barrel holding opening portions 143 are formed in the cylindrical portions 142, and the substrate portion 141 has a side portion formed with a grip notch portion 144. The cylindrical portions 142 and the barrel holding opening portions 143 have an inner diameter larger than the outer diameter of a maximum diameter portion of the syringe assembly 10 to be held but not larger than a flange portion 23 of the syringe assembly 10 to be held.

Therefore, as illustrated in FIG. 15, the syringe assembly 10 penetrates cylindrical portion 142, and the syringe assembly 10 is suspended by the flange 23 from the barrel holding opening portion 143. As illustrated in FIG. 15, the lower end (distal end of the seal cap 3) of the syringe assembly 10 held by the barrel holder 104 does not make contact with the bottom surface of the container body 102. That is, the bottom surface of the container body 102 and the lower end (distal end of the seal cap 3) of the syringe assembly 10 held by the barrel holder 104 are separated, and circulation of steam is not obstructed. A material of the barrel holder 104 preferably includes heat resistance (120° C. or more) for high-pressure steam sterilization.

The sheet-shaped lid member 103 desirably includes a member having a sterilization gas circulation property, not passing microparticles such as bacteria or viruses, but passing a sterilization gas such as steam or ethylene oxide gas, for high-pressure steam sterilization or ethylene oxide gas sterilization. Further, the container body 102 is preferably configured to be heat-sealed. The sheet-shaped lid member 103 preferably employs, for example, a synthetic resin nonwoven fabric, specifically, a non-woven fabric including a synthetic resin material such as a polyolefin known as Tyvek (registered trademark), a synthetic resin porous membrane, or the like.

The sheet-shaped lid member 103 has a peripheral edge releasably heat-sealed to the heat-sealing protrusion 125 provided at the annular flange 124 of the container body 102. In the first embodiment, the outer edge of the sheet-shaped lid member 103 is not heat-sealed to the annular flange 124 of the container body 102, and the sheet-shaped lid member 103 is readily released. Further, a projection portion 125a provided at a corner of the heat-sealing protrusion 125 functions as a release start portion. The sheet-shaped lid member 103 is preferably has a thickness of approximately 0.05 to 1.00 mm, especially, approximately 0.10 to 0.50 mm.

In the first embodiment, the ventilation portion is provided in the sheet-shaped lid member 103, but is not limited to this configuration, and may be provided in the container body 102.

A syringe assembly according to an embodiment of the present invention includes the following.

(1) A syringe assembly including a barrel including a barrel body portion, a cylindrical barrel end portion provided at a distal end of the barrel body portion and having an annular head portion and an annular recessed portion formed at a proximal end of the annular head portion, and a puncture needle having a puncture needle tip at a distal end and having a proximal end fixedly inserted into the barrel end portion, and a seal cap mounted to the barrel, wherein the seal cap includes a closed distal end portion, an open proximal end portion, a hollow portion having a barrel end storage portion positioned distally from the open proximal end portion and storing the barrel end portion, and a puncture needle storage portion extending from a distal end of the barrel end storage portion and storing the puncture needle, an insertion allowing portion for receiving the insertion of the puncture needle tip of the puncture needle stored in the puncture needle storage portion, and a projection portion formed on the inner surface of the barrel end storage portion, wherein the projection portion has a top portion, and a distal inclined portion extending distally from the top portion and having a projection height reduced distally, and wherein, in the syringe assembly, the barrel end portion of the barrel is mounted with the seal cap, the puncture needle tip is inserted into the insertion allowing portion of the seal cap, the projection portion of the seal cap and the annular recessed portion of the barrel end portion are engaged with each other, and the distal inclined portion is hermetically pressed against the outer surface of the annular head portion.

Since the seal cap has such a projection portion, when the pressure difference is generated inside and outside the seal cap, specifically, the pressure in the seal cap is increased relative to the pressure outside the seal cap, an engagement force between the projection portion, and the annular head portion and the annular recessed portion prevents the removal of the seal cap from the barrel.

An embodiment of the syringe assembly may include the following.

(2) The syringe assembly according to (1), wherein an inner surface of the barrel end storage portion is hermetically pressed against an outer surface of the annular head portion.

(3) The syringe assembly according to (1), wherein an inner surface of the barrel end storage portion is hermetically pressed against an outer surface of the annular head portion, and the distal inclined portion is hermetically pressed against an outer surface of the annular recessed portion.

(4) The syringe assembly according to any of (1) to (3), wherein the annular recessed portion includes a tapered reduced diameter portion having a diameter reduced proximally.

(5) The syringe assembly according to any of (1) to (4), wherein the projection portion of the seal cap is an annular projection portion.

(6) The syringe assembly according to any of (1) to (5), wherein the seal cap has a removal resistance from the barrel of 1.5 to 20 N.

(7) The syringe assembly according to any of (1) to (6), wherein a portion of the distal inclined portion, hermetically pressed against the outer surface of the annular head portion has a length in the axial direction of the annular head portion of 0.1 to 2.0 mm.

(8) The syringe assembly according to any of (1) to (7), wherein the projection portion has a proximal inclined portion extending from the top portion toward a proximal end, and having a projection height gradually reduced toward the proximal end.

(9) The syringe assembly according to any of (1) to (8), wherein the syringe assembly is subjected to high-pressure steam sterilization or ethylene oxide gas sterilization.

A prefilled syringe according to an embodiment of the present invention includes the following.

(10) A prefilled syringe including the syringe assembly according to any of (1) to (9), a gasket stored in the barrel and slidably moveable in the barrel in a liquid-tight manner, and a medical solution filled in a space formed by the barrel and the gasket.

A syringe assembly package body according to an embodiment of the present invention includes the following.

(11) A syringe assembly package body including a container body having an upper opening and having shape retainability, a barrel holder configured to hold a plurality of the syringe assemblies, the plurality of the syringe assemblies according to any of (1) to (10) held by the barrel holder and stored in the syringe assembly package body, and a releasable sheet-shaped lid member configured to hermetically seal the upper opening of the container body, wherein the package body further includes a ventilation portion provided in the container body or the lid member and having bacterial impermeability and a sterilization gas circulation property, and the package body is subjected to high-pressure steam sterilization or ethylene oxide gas sterilization.

What is claimed is:
1. A syringe assembly comprising:
    a barrel including:
        a barrel body portion,
        a cylindrical barrel end portion disposed at a distal end of the barrel body portion, the cylindrical barrel end portion including:
            an annular head portion, and an annular recessed portion that extends proximally from a proximal end of the annular head portion, and a puncture needle having a puncture needle tip at a distal end of the puncture needle and having a proximal end fixedly inserted into the barrel end portion; and a seal cap mounted to the barrel, the seal cap including:
a closed distal end portion,
an open proximal end portion,
a hollow portion including (i) a barrel end storage portion positioned distally from the open proximal end portion, the barrel end storage portion being configured to store the barrel end portion, and (ii) a puncture needle storage portion extending from a distal end of the barrel end storage portion, the puncture needle storage portion configured to store the puncture needle,
an insertion portion configured to receive the puncture needle tip of the puncture needle stored in the puncture needle storage portion, and
a projection portion formed on an inner surface of the barrel end storage portion,
wherein the projection portion has a top portion and a distal inclined portion extending distally from the top portion and having a projection height that decreases in a distal direction from the top portion,
wherein the annular recessed portion comprises (i) a tapered reduced diameter portion having a diameter that decreases toward a proximal end of the annular recessed portion, or (ii) a reduced diameter portion formed by a step between the annular recessed portion and the proximal end of the annular head portion, and
wherein, when the seal cap is mounted on the barrel end portion of the barrel such that the puncture needle tip is inserted into the insertion portion of the seal cap, the projection portion of the seal cap and the annular recessed portion of the barrel end portion are engaged with each other, and the distal inclined portion extends distally from the annular recessed portion and is hermetically pressed against an outer surface of the annular head portion.

2. The syringe assembly according to claim 1, wherein the inner surface of the barrel end storage portion, on a distal end side from the distal inclined portion, is hermetically pressed against the outer surface of the annular head portion.

3. The syringe assembly according to claim 1,
wherein the inner surface of the barrel end storage portion is hermetically pressed against the outer surface of the annular head portion, and
wherein the distal inclined portion is hermetically pressed against an outer surface of the annular recessed portion.

4. The syringe assembly according to claim 1, wherein the projection portion of the seal cap is an annular projection portion.

5. The syringe assembly according to claim 1, wherein the seal cap has a removal resistance from the barrel of 1.5 to 20 N.

6. The syringe assembly according to claim 1, wherein the projection portion has a proximal inclined portion extending from the top portion toward a proximal end and having a projection height that gradually decreases in a proximal direction from the top portion.

7. The syringe assembly according to claim 1, wherein the syringe assembly is a high-pressure steam sterilized or ethylene oxide gas sterilized syringe assembly.

8. The syringe assembly according to claim 1, further comprising:
a gasket disposed in the barrel, the gasket being slidably moveable in the barrel in a liquid-tight manner; and
a medical solution provided in a space formed by the barrel and the gasket.

9. The syringe assembly according to claim 1, wherein a portion of the distal inclined portion that is hermetically pressed against the outer surface of the annular head portion has a length in an axial direction of the annular head portion of 0.1 to 2.0 mm.

10. The syringe assembly according to claim 1,
wherein the hollow portion further includes a barrel end introduction portion formed from the open proximal end portion of the seal cap to the proximal end of the barrel end storage portion, and
wherein the barrel end introduction portion extends with substantially a constant inner diameter which is larger than a maximum inner diameter of the barrel end storage portion and larger than the outer diameter of the annular head portion.

11. The syringe assembly according to claim 1, wherein the distal inclined portion is hermetically pressed against an outer surface of the annular recessed portion.

12. The syringe assembly according to claim 11, wherein the projection portion of the seal cap is an annular projection portion.

13. The syringe assembly according to claim 12, wherein the seal cap has a removal resistance from the barrel of 1.5 to 20 N.

14. The syringe assembly according to claim 13, wherein the projection portion has a proximal inclined portion extending from the top portion toward a proximal end and having a projection height that gradually decreases in a proximal direction from the top portion.

15. The syringe assembly according to claim 14, wherein the syringe assembly is a high-pressure steam sterilized or ethylene oxide gas sterilized syringe assembly.

16. The syringe assembly according to claim 15, wherein a portion of the distal inclined portion that is hermetically pressed against the outer surface of the annular head portion has a length in an axial direction of the annular head portion of 0.1 to 2.0 mm.

17. The syringe assembly according to claim 16,
wherein the hollow portion further includes a barrel end introduction portion formed from the open proximal end portion of the seal cap to the proximal end of the barrel end storage portion, and
wherein the barrel end introduction portion extends with substantially a constant inner diameter which is larger than a maximum inner diameter of the barrel end storage portion and larger than the outer diameter of the annular head portion.

18. A syringe assembly package body comprising:
a container body having an upper opening and having shape retainability;
a plurality of the syringe assemblies of claim 1;
a barrel holder configured to hold the plurality of syringe assemblies;
a releasable sheet-shaped lid member configured to hermetically seal the upper opening of the container body; and
a ventilation portion disposed in the container body or the lid member, the ventilation portion having bacterial impermeability and being configured for sterilization gas circulation, wherein the plurality of syringe assemblies are held by the barrel holder and stored in the syringe assembly package body, and wherein the syringe assembly package body is a high-pressure steam sterilized or ethylene oxide gas sterilized syringe assembly package body.

19. The syringe assembly according to claim 1, wherein the annular head portion comprises a distal end surface that faces in a distal direction, an opening in the distal end surface, and a recess extending proximally from the opening.

* * * * *